United States Patent [19]
Levy et al.

[11] Patent Number: 4,762,855
[45] Date of Patent: Aug. 9, 1988

[54] NOVEL PHARMACEUTICAL COMPOSITIONS IMPROVING OXYGENATION OF THE BRAIN AND A PROCESS FOR THEIR PRODUCTION

[75] Inventors: Jean-Claude Levy, Vincennes; Pierre Bessin, Chilly-Mazarin; Jean-Pierre Labaune, Moulignon par Ponthierry, all of France

[73] Assignee: Albert Rolland S.A., Paris, France

[21] Appl. No.: 926,895

[22] Filed: Nov. 4, 1986

[30] Foreign Application Priority Data

Nov. 5, 1985 [FR] France ................................ 85 16359

[51] Int. Cl.⁴ ............................................. A61K 31/135
[52] U.S. Cl. ..................................................... 514/651
[58] Field of Search ........................................ 514/651

[56] References Cited
PUBLICATIONS

Chem. Abst.—102—197462f (1985).

Primary Examiner—Stanley J. Friedman
Attorney, Agent, or Firm—Omri M. Behr

[57] ABSTRACT 2,2-Bisphenoxy-dimethyl-aminoethane to improve brain disfunction.

2 Claims, 1 Drawing Sheet

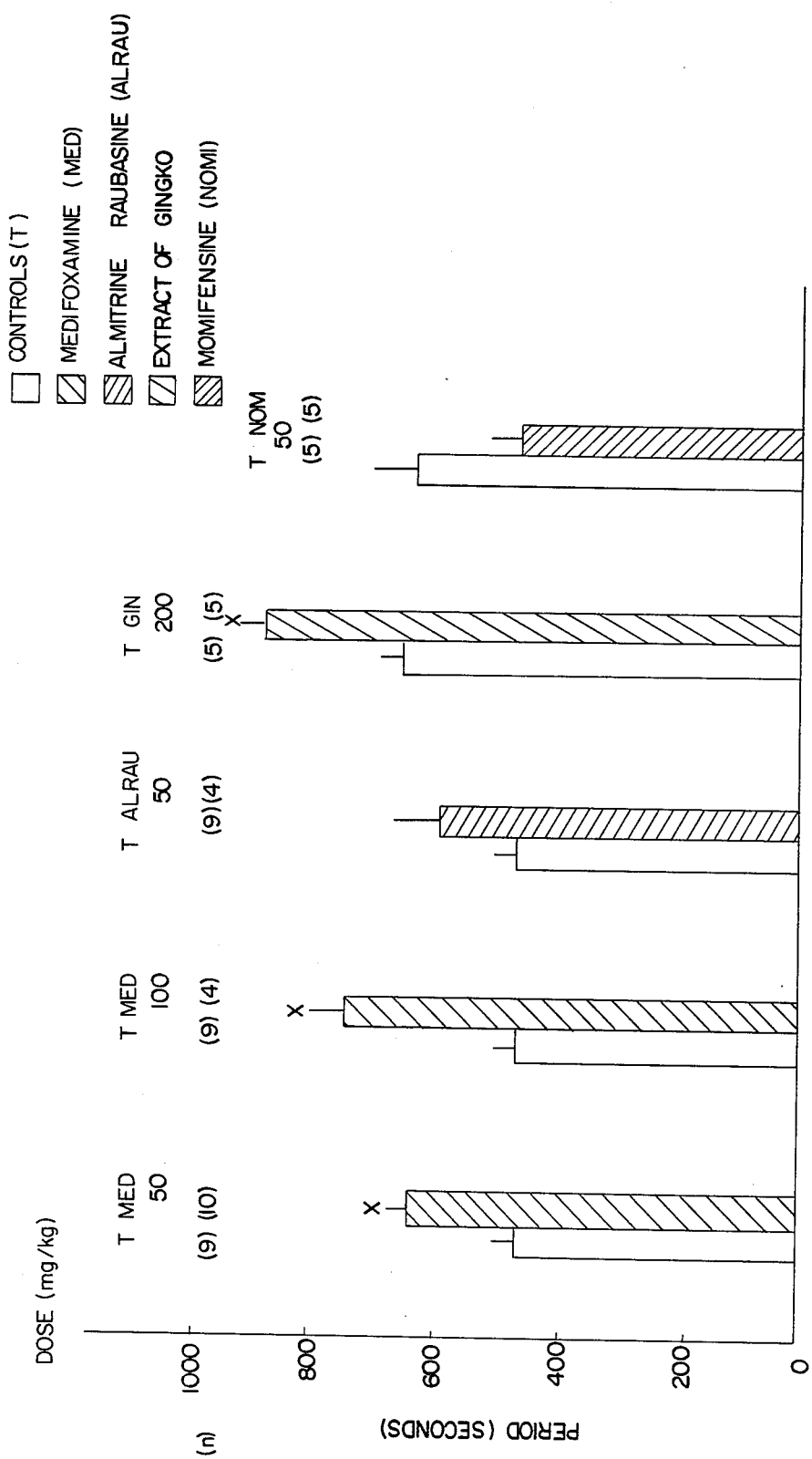

NOVEL PHARMACEUTICAL COMPOSITIONS IMPROVING OXYGENATION OF THE BRAIN AND A PROCESS FOR THEIR PRODUCTION

This invention relates to novel pharmaceutical compositions intended to prevent or to amend the noxious effects due to insufficient oxygenation of the brain tissues.

One of the most striking effects of the ageing lies in the decrease of the blood brain circulation and consequently a lessening of the transport to the brain cells of the requisited oxygen for maintaining a normal metabolism of glucose. This lessening induces a progressive atrophy of these cells and a significant loss of functional cells.

This is why it appeared highly desirable to provide such as kind of medicine, able to counteract the effects of ageing.

In its principle this kind of medicine lies in the improvement in the functioning of the brain cells, in a major resistance of them in spite of the insufficient carriage of oxygen and in the increase of the blood brain output. The brain cells due to this new king of medicine, are able to better resist to hypoxia or maintain a normal function, even when the carriage of oxygene is decreasing at any great extent.

This invention provides novel pharmaceutical compositions intended to improve the oxygenation of brain tissues which contain a neurologically-active amount of 2,2-diphenoxy-dimethylaminoethane or an acid addition salt thereof with a mineral or organic acid, in admixture or conjunction with an inert non-toxic pharmaceutically-acceptable carrier or vehicle.

This action due to the pharmaceutical compositions containing such active ingredient (2,2-diphenoxy-N,N-dimethylaminoethane is known under the International Denomination MEDIFOXAMINE) appears to be even more surprising than other compounds such as Nomifensine or Amineptine which are known to exert an action similar to Medifoxamine on the dopaminergic system, are devoid of such properties.

This kind of action is also found—in a transient manner- in a medicine consisting of an extract of Gingko biloba which is known to improve the brain blood flow on one side and in another medicine consisting of a mixture of a respiratory analeptic (almitrine) and an adrenolytic substance (Raubasine).

This anti-anoxic action cannot presumably correlated to any known pharmacological property.

According to this invention the neurologically-active amount of 2,2-diphenoxy-dimethylaminoethane in the pharmaceutical compositions ranges from 50 to 400 mg per unit dosage. Further the active ingredient is used in the form of an insoluble compound or of a compound which may not be dispersed in the aqueous medium, the needed amounts are somewhat higher and broadly ranging from 250 to 750 mg per unit dosage.

Moreover depending of the route of administration, the needed amounts of active ingredient may be more limited or more extended. More particularly through the oral way the amounts of Medifoxamine are higher than that required for the parenteral way.

These pharmaceutical compositions are intended for the use by the parenteral way, the oral way, the rectal way or the percutaneous way. In this respect it may be cited the uncoated or coated tablets, the dragees, the soft gelatine capsules, the capsules, the pills, the microgranules, the drops, the drinkable solutions or suspensions, the injectible solutions, the suppositories and the solutions in a polar medium for percutaneous use. The most preferred forms are the coated tablets, the soft gelatine capsules and the dragees.

The carriers or vehicles which are the most suitable for these pharmaceutical compositions are water, salines, the starches, microcrystalline cellulose, di- or tri-calcium phosphate, magnesium phosphate, calcium sulphate, lactose, colloidal silica, alkylcelluloses, magnesium stearate, talc, carboxymethylcelluloses as those sold under the trade name AVICEL or ACDISOL, carboxymethylstarches, the solid or liquid at room temperature, polyvinylpyrrolidones, solid or liquid polyethyleneglycols, polyethyleneglycol stearates or Cocoa Butter.

The daily doses may vary within broad limits depending on the weight of the patient, the therapeutic use and the oldness of the disease to be cured. The daily dose may hence range from 150 to 800 mg of Medifoxamine divided in one or three takings during the day.

This invention also relates to a process for producing the pharmaceutical compositions in tended to improve the brain oxygenation which consists in that a neurologically-active amount of 2,2-diphenoxy-N,N-dimethylaminoethane or the corresponding amount of an acid addition salt thereof which a mineral or organic acid is admixed or put in conjunction with one or several inert non-toxic pharmaceutically-acceptable carriers or vehicles, according to the methods known in the pharmacotechnology.

The following examples are merely intended to illustrate the invention without limiting it.

EXAMPLE I

| Sectile tablets containing 100 mg of 2,2-diphenoxy-N,N—dimethylaminoethane as the fumarate: | |
|---|---|
| 2,2-diphenoxy-N,N—dimethylaminoethane fumaric acid salt | 100 g |
| dicalcium phosphate | 140 g |
| microcrystalline cellulose | 60 g |
| corn starch | 16 g |
| magnesium stearate | 4 g | for 1 000 sectile tablets finished at the average weight of 0.320 g.

EXAMPLE II

Pharmacological studies on the pharmaceutical compositions of this invention:

A. Action of Medifoxamine on the brain metabolism in the anesthetized dog

This study has been carried out in batches of 4 dogs anesthetized with 30 mg/kg Mebubarbital administered intravenously. The biochemical determinations are carried out at the level of the vertebral arter and the jugular vein. The measures of the output of the vertebral arter, the control of the arterial $PO_2$ and of the consumption of oxygen in the brain have been conducted before and after injection of a dose of 10 mg/kg Medifoxamine. The measures which have been retained as valid are those of the peaks of activity for the various selected parameters.

Results

After intravenous injection of a doses of 10 mg/kg of Medifoxamine three marked actions are evidenced:

(1) Increase of the arterial $PO_2$, increasing from:

71 (±8) mm Hg to 91,4 (±15) mm Hg (2) Increase of the output of the vertebral arter, increasing from:

85 (±26) ml/min to 210 (±92) ml/min (3) Tendency to an increase of the consumption of oxygen.

| $PO_2$ (maximal peak) mmHg | | Output (maximal peak) ml/min | | Consumption in oxygen (maximal peak) vol/min | |
|---|---|---|---|---|---|
| Before | After | Before | After | Before | After |
| 72 | 90 | 50 | 325 | 0,608 | 1,781 |
| 80 | 116 | 120 | 225 | 0,4 | 7,4 |
| 72 | 78 | 80 | 175 | 1,24 | 0,30 |
| 58 | 81 | 75 | 75 | 0,67 | 1,92 |
| 73 | 92 | 100 | 250 | — | — |
| 71±8 | 91,4±15 | 85±26 | 210±92 | 0,73±0,36 | 2,85±3,41 |
| $\alpha < 0,05$ | | $\alpha < 0,05$ | | NS | | doses of 200 mg/kg increases the period of survival of the animals in a statistically-significant manner.

Comparatively a known pharmaceutical composition consisting of a mixture of Almitrine and Raubasine at a doses of 50 mg/kg also extends the survival time but the difference in comparison with the controls is not statistically-significative. Also Nomifensine—a known antidepressive agent—at a doses of 50 mg/kg is devoid of any action.

2. Administration of the products by oral way

Medifoxamine at a doses of 100 mg/kg and the pharmaceutical composition consisting of a mixture of Almitrine and Raubasine at a doses of 100 mg/kg in a statistically-significative manner increase the survival time.

The extract of Gingko biloba at a doses of 300 mg/kg also extends the survival period but the difference as regard to the controls is not statistically-significative.

Nomifensine (50 mg/kg) and Amineptine (100 mg/kg) do not show any action. The following tables summarize the obtained results.

| SEARCH OF A PROTECTIVE ACTION OF MEDIFOXAMINE AGAINST HYPOBAR HYPOXIA IN THE MALE RAT AFTER ADMINISTRATION BY ORAL WAY | | | |
|---|---|---|---|
| CONTROLS CMC 1% 1 ml/100 g survival in second | MEDIFOXAMINE 100 mg/kg CMC 1% 1 ml/100 g P.O survival in second | EXTRACT DE GINGKO 300 mg/kg CMC 1% 1 ml/100 g P.O survival in second | NOMIFENSINE 50 mg/kg CMC 1% 1 ml/100 g P.O survival in second |
| 805 | 810 | 550 | 375 |
| 180 | 850 | 690 | 770 |
| 910 | 920 | 750 | 495 |
| 435 | 1035 | 890 | 590 |
| 730 | 1010 | 570 | 240 |
| 630 | 770 | 550 | 510 |
| 615 | 550 | 810 | 525 |
| 858 | 765 | 735 | 440 |
| 405 | 705 | 750 | 270 |
| 660 | 540 | 510 | 570 |
| 630 | 750 | | |
| 500 | 645 | | |
| 615 | 620 | | |
| 525 | 690 | | |
| 610 | 930 | | |
| 665 | 790 | | |
| 570 | 570 | | |
| 540 | 450 | | |
| 525 | 570 | | |
| 465 | — | | |
| 594 ± 37 | 735 ± 38 | 680 ± 41 | 479 ± 50 |
| Test Bartlett $X_3^2 = 0,80$ NS | | | |
| t of Dunnett $F_{55}^3 = 6,51$ "S" | $t_{55} = 2,79$ "S" | $t_{55} = 1,42$ "N.S" | $t_{55} = 1,88$ "N.S" |
| | $0,01 < \alpha < 0,05$ | | |

Conclusively these results show that potentially Medifoxamine exerts a beneficial action against brain hypoxia in the dogs.

B. Search of a protective action of Medifoxamine against hypobar hypoxia in the male rat Medifoxamine and several reference products have been administered by intraperitoneous way or by oral way to rats 30 min or 60 min prior the entry in a hypobar box. The pressure inside the box is 180 mm Hg. The period of survival is determined taking account of the arrest of breathing.

1 Administration of the products by intraperitoneal way

Medifoxamine has been compared to the action of an extract of Gingko biloba. Medifoxamine at a doses of 50 and 100 mg/kg and the extract of Gingko biloba at a

BRIEF DESCRIPTION OF DRAWING

The drawing shows a search of a protective/action of medifoxamine against hypobor hypoxia in the male rat after administration by intraperitoneal way.

What we claim is:

1. A method of improving brain disfunction in elderly patients due to reduction in brain oxygenation which comprises administering to such patients showing a decrease in the cerebral vascular output a safe but effective amount of an active compound selected from the group consisting of 2,2-bisphenoxydimethylaminoethane or an acid addition salt thereof.

2. A method of claim 1, wherein the amount of active component ranges from 150 to 800 mg. per day.

* * * * *